US008202090B2

(12) United States Patent  
Shachar

(10) Patent No.: US 8,202,090 B2  
(45) Date of Patent: Jun. 19, 2012

(54) ARTIFICIAL TOOTH MEDICATING APPARATUS FOR CONTROLLING, REGULATING, SENSING, AND RELEASING MEDICAL AGENTS INTO THE BODY

(75) Inventor: Yehoshua Shachar, Santa Monica, CA (US)

(73) Assignee: Pharmaco-Kinesis Corporation, Inglewood, CA (US)

( * ) Notice: Subject to any disclaimer, the term of this patent is extended or adjusted under 35 U.S.C. 154(b) by 692 days.

(21) Appl. No.: 12/040,853

(22) Filed: Feb. 29, 2008

(65) Prior Publication Data

US 2009/0220563 A1 Sep. 3, 2009

(51) Int. Cl.
- *A61C 8/00* (2006.01)
- *A61C 19/06* (2006.01)
- *A61M 37/00* (2006.01)

(52) U.S. Cl. .................. 433/174; 433/80; 604/891.1

(58) Field of Classification Search .............. 433/80, 433/172–176; 604/288.01–288.04, 890.1, 604/891.1, 892.1, 131, 134, 135, 154, 155, 604/156; 128/DIG. 12; 424/422, 423, 435; 368/204

See application file for complete search history.

(56) References Cited

U.S. PATENT DOCUMENTS

| | | | | |
|---|---|---|---|---|
| 3,692,027 A * | 9/1972 | Ellinwood, Jr. | ............ | 604/891.1 |
| 4,013,074 A * | 3/1977 | Siposs | ....................... | 604/891.1 |
| 4,523,910 A * | 6/1985 | Makovich | ....................... | 433/80 |
| 4,563,175 A * | 1/1986 | LaFond | ............................ | 604/155 |
| 4,701,180 A * | 10/1987 | Kelly et al. | ................ | 604/891.1 |
| 4,959,052 A * | 9/1990 | Cox | .................................. | 604/77 |
| 5,083,908 A * | 1/1992 | Gagnebin et al. | ........... | 417/477.1 |
| 5,135,498 A * | 8/1992 | Kam et al. | ..................... | 604/140 |
| 5,249,937 A * | 10/1993 | Aubert | .......................... | 417/475 |
| 5,584,688 A * | 12/1996 | Sakuma et al. | .................. | 433/81 |
| 5,752,930 A * | 5/1998 | Rise et al. | ...................... | 604/508 |
| 5,837,276 A * | 11/1998 | Cheikh | ........................... | 424/423 |
| 6,162,238 A * | 12/2000 | Kaplan et al. | ................. | 606/201 |
| 7,172,594 B2 * | 2/2007 | Biscup | ......................... | 606/86 A |
| 2004/0147906 A1 * | 7/2004 | Voyiazis et al. | ............. | 604/891.1 |
| 2005/0256549 A1 * | 11/2005 | Holzer | ............................. | 607/35 |
| 2006/0036253 A1 * | 2/2006 | Leroux et al. | ................... | 606/73 |
| 2007/0005042 A1 * | 1/2007 | Anderson | ................... | 604/890.1 |
| 2007/0005043 A1 * | 1/2007 | Anderson | ................... | 604/890.1 |
| 2007/0106138 A1 * | 5/2007 | Beiski et al. | ................... | 600/349 |
| 2007/0154336 A1 * | 7/2007 | Miyazaki et al. | .............. | 417/474 |
| 2008/0215010 A1 * | 9/2008 | Silver et al. | ................... | 604/175 |
| 2009/0171375 A1 * | 7/2009 | Coe et al. | ....................... | 606/151 |

* cited by examiner

*Primary Examiner* — Todd Manahan  
*Assistant Examiner* — Michael R Ballinger  
(74) *Attorney, Agent, or Firm* — Marcus Dawes; Daniel Dawes

(57) ABSTRACT

An artificial tooth apparatus for dispensing medicating agents to the body through the patient's jaw bone comprising a mechanical movement and kinetic mainspring winder, a tourbillon mechanism, a electronic regulator, and a pump mechanism arranged and configured to allow any medicating agent to be dispensed from the apparatus in a highly controlled and regulated manner according to input received by the electronic regulator and the patient's specific pharmacokinetic and pharmacodynamic attributes. Multiple artificial teeth or a comprehensive bridge with several chambers may be used in cases where a polypharmaceutical approach is needed.

3 Claims, 18 Drawing Sheets

ARTIFICIAL TOOTH MEDICATING APPARATUS FOR CONTROLLING, REGULATING, SENSING, AND RELEASING MEDICAL AGENTS INTO THE BODY

BACKGROUND OF THE INVENTION

1. Field of the Invention

The invention relates to the field of administration of a medicating agent.

2. Description of the Prior Art

The existing art of dispensing medicating agents into the body is guided by the general formulas defining basic pharmacokinetic parameters such as absorption, distribution, and elimination from the body of the drug or agent. These parameters influence the maximum (peak) concentration and the area under the concentration-time-curve after a single oral dose.

Parameters such as the absorption rate constant which expresses the speed of absorption and the amount of fluid required to place the drug at a given concentration in the blood or plasma, are used to estimate the dose taking into account the elimination rate and clearance of the drug via renal, metabolic, and the biological half life of the medicating agents. These parameters are also used in calculating the dose given to the patient in conjunction with other outside factors such as the patient's clinical state, severity of the disorder, presence of a concurrent disease, and the use of other drugs.

The parametric definition of drug intake has been based on a statistical model which assumes the normal Gaussian distribution. This scenario is tailored to the patient's needs and the intake of medicating agents is an approximation that assumes an error limited only by the toxicity of the agent and its narrow margin of safety.

What is needed is an improvement in the art of medication dispensation for cases with a history of long term illness such as affective bipolar disorder, illnesses with symptoms including a spectrum of manic states, pain such as migraines, and in general neurological as well as psychiatric disorders.

BRIEF SUMMARY OF THE INVENTION

The present invention describes a method by which specific adjustments and modifications are introduced to alter the multiple parametric mechanisms of drug intake based on patient-specific conditions. The invention provides the mechanism of sensory feedback to create a closed-loop approach in which the medicating agent and the body's metabolites are a part, thereby improving the art of medication and providing a patient-specific historical life-chart. This approach minimizes the error associated with the statistical Gaussian distribution associated with other prior art methods. The use of the invention will dramatically improve the course of treating chronic illnesses and improve patient compliance with a drug regimen.

The following invention deals with the development of a drug dispensing method and apparatus embedded in a prosthetic tooth, or dental appliance, specifically, but not limited to, in the space of an extracted wisdom tooth. The entire system is preferably embedded inside an artificial tooth, and the tooth is implanted in the jaw-bone of a patient. The system is miniaturized and relies on the ability of a mechanical movement-kinetic mainspring winder or self-winding mechanism to supply the required energy needed to drive a plunger which dispenses the medicating agent via a perforated delivery duct. The self-winding mechanism in turn is driven by the normal movements of the jaw. The medication is replenished when necessary by a clinician or a physician using a refill dispenser.

The present invention is directed to an implanted apparatus to dispense medicating agents in a regulated and controlled manner. It is therefore an object of this invention to provide a system for dispensing medicating agents while controlling, regulating, sensing, and providing an "on-demand" option for the release of medicating agents to the patient's body by employing a tooth medicating apparatus within a cavity of an artificial tooth implanted in the mouth of a patient. The invention is effective, easy to use, and implantable preferably in the location of either the molar teeth (multicuspidate or grinders) or wisdom teeth (dentes sapientive). However, it is to be understood that the invention can also be employed in any position in the body where kinetic motion is available to power the pumping action of the dispenser.

Once implanted, the illustrated embodiment emulates the pharmacokinetic parameters of the medicating agent's dispensation through the use of the apparatus, namely the measurement of the absorption, distribution, and elimination rates of the agent by employing a watch-like mechanism forming the kinetic mainspring winder which drives a plunger in a controlled fashion which dispenses the medicating agent. The watch-like mechanism uses the escapement mechanism to provide a constant real time delivery of medicating doses when activated. The use of timers in connection with the measured delivery rate also provides for an involuntary method of enhancing compliance (that is, to which degree a patient follows a treatment regimen) in intake of medicating agents under a strict, uniform, and controlled situation.

Specifically the watch-like mechanism assists in the dispensing of medicating agents by employing a mechanical movement and a kinetic mainspring winder so as to continuously regenerate energy to drive the plunger (pump mechanism) by the use of the kinetic winder converted from jaw movements. This mechanism then timely releases the medicating agents as specified by this embodiment of the invention to regulate the rate of change of the escarpment and its subsequent assembly to define the rate of release of the medicating agent via the perforated delivery duct.

A tourbillon mechanism is employed to precisely regulate the escapement mechanism and to accurately release the energy generated by the drive wheel to activate the movement of the plunger which releases the medicating agent to a self-regulating pump which delivers the agent to the body.

The mechanism of the present invention also includes a mainspring barrel escapement assembly, balance assembly, hairspring, and a wheel and pinion assembly. Together these pieces when used in conjunction with the tourbillon and the mechanical movement of the kinetic mainspring winder form an effective system to deliver the medicating agent at a specific rate of release.

A unidirectional valve using a refill dispenser is also present so as to replenish the medicating agent in the reservoir of the tooth medicating apparatus (TMD).

In summary, the illustrated embodiment is an implantable apparatus capable of delivering medicating agents to the body comprising a kinetic mainspring winder, a mechanical movement coupled to and driven by the kinetic mainspring winder; and a pump mechanism coupled to and driven by the mechanical movement, the pump mechanism delivering the medicating agents to the body at a time-measured rate.

The kinetic mainspring winder is an implant in a jaw bone.

The energy supplied to the kinetic mainspring winder is obtained from movement of the jaw bone.

The pump mechanism comprises a refillable reservoir for holding a medicating agent.

The pump mechanism further comprises an implant screw with a perforated delivery duct coupled to the apparatus for dispensing medicating agents into or near the adjacent blood vessels in the jaw bone.

The apparatus comprises a jaw implant, the jaw having a jaw plane and further comprising a means for positioning the rotor of the kinetic mainspring winder at a 5 degree inclination relative to the jaw plane.

The apparatus further comprises a timer and clutch mechanism coupled between the mechanical movement and the pump mechanism for selective dispensing the medicating agent into the body.

In another embodiment the invention includes an implantable apparatus capable of delivering at least one medicating agent to the body comprising a Faraday generator powered by jaw movements, a electrical power circuit coupled to the Faraday generator for storing electric energy generated by the Faraday generator, an electrically powered pump coupled to the electrical power circuit for delivering the medicating agents to the body, at least one sensor for providing a feedback signal related to the medicating agent, and a regulator coupled to the electrical power circuit and coupled to and controlling the pump, the regulator coupled to the sensor and controlling the pump based on the feedback signal.

The regulator comprises a multiplexer, a signal amplifier having an input coupled to the multiplexer, an analog-to-digital converter having an input coupled to the signal amplifier, a microcontroller having an input coupled to the analog-to-digital converter, and a plurality of sensor elements coupled to the multiplexer including at least one of: a free ion detector; a pulse rate sensor; a blood chemistry analyzer; and/or a body temperature sensor.

The regulator further comprises a ROM, RAM, or NVM microchip or any combination thereof coupled to the microcontroller for the purposes of data storage.

The illustrated embodiment of the invention is also a method for dispensing medicating agents into a body of a patient using an implant in a jaw bone of the patient comprising the steps of storing at least one medicating agent in the implant; storing energy from normal jaw movements; selectively converting the stored energy into controlled pumping of the at least one medicating agent stored in the implant in the jaw bone, to selectively dispense the medicating agent stored in the implant into a blood flow path in the jaw bone at a controlled rate.

The method further comprises the step of sensing at least one sensed biological input or user controlled input, and selectively controlling dispensing a medicating agent stored in the implant into the blood flow path in the jaw bone by at least one sensed biological input or user controlled input.

The method further comprises the step of providing a plurality of implants in the jaw bone for a polypharmacy treatment thus allowing a combination of therapies to be controlled, tailored, and regulated by the patient's specific pharmacokinetic or pharmacodynamic attributes.

The method further comprises the step of implanting a bridge into the jaw with multiple chambers where a polypharmacy regimen is required thus allowing a combination of therapies to be controlled, tailored, and regulated by the patient's specific pharmacokinetic or pharmacodynamic attributes.

The method includes the embodiment where the apparatus is used as a form of automatic long term pharmacological therapy for a plurality of medicating agents and to improve patient compliance with a specified drug maintenance program.

The method further comprises the step of dispensing medicating agents on demand via the use of selected timers or triggers.

The method further comprises the step of sensing PKC concentration in the blood and timely releasing a medicating agent in proportion to the PKC concentration in the blood thus obtaining an effective mechanism for bipolar disorder.

The method further comprises the step of evaluating different pharmacokinetic and pharmacodynamics behavior of a medicating agent including absorption, distribution, and elimination rates of the medicating agent, dose, cycle, and circadian time effects to improve effectiveness and efficiency.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 9 further depicts other possible implant positions for the artificial tooth including an orthodontic bridge for use in a polypharmacy medicating configuration.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
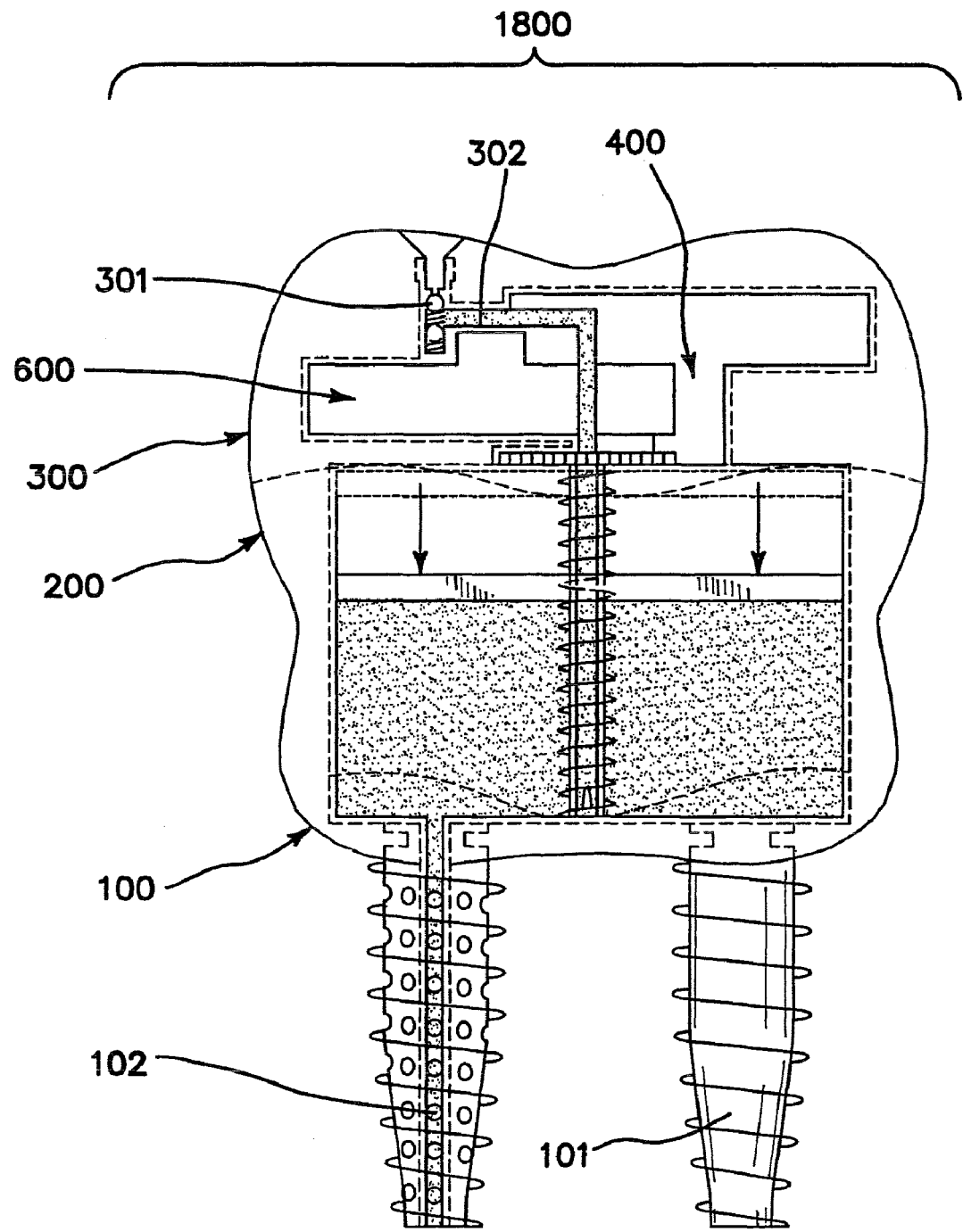
FIG. 1 is a side cross-sectional view of a mechanical embodiment of the tooth medicating apparatus (TMD) depicting the main assemblies forming the dispenser, pump mechanism and the kinetic winder.

The illustrated embodiment of the invention is an apparatus and a method for using an artificial tooth assembly, generally denoted in FIG. 1 by reference numeral 1800, to dispense medicating agents to the body. The apparatus 1800 is useful for controlling the amount and duration a particular medicating agent(s) is released into the body when treating any number of physical or psychological ailments.

Figure 2:
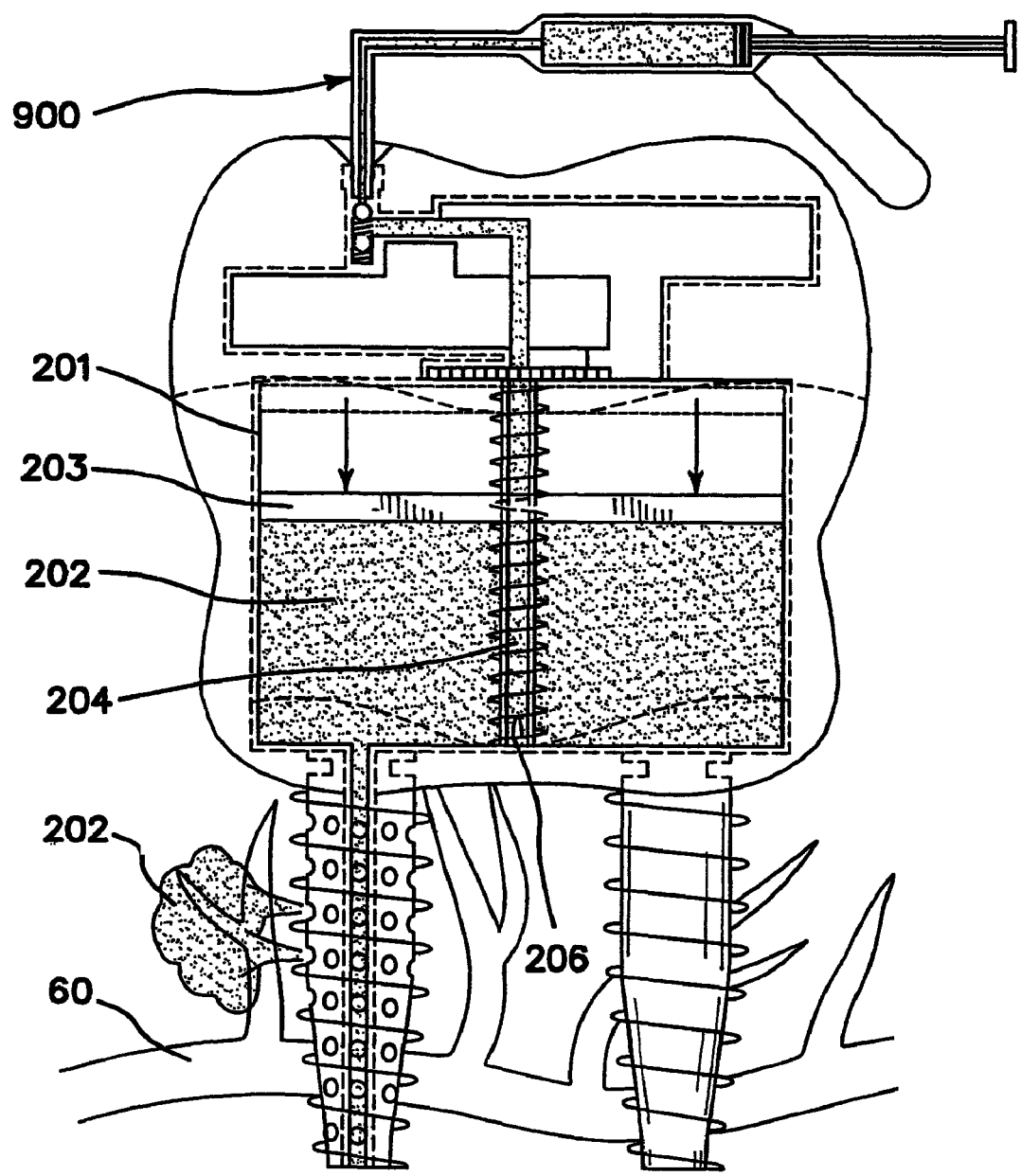
FIG. 2 is a side cross-sectional view depicting the tooth medicating apparatus with the refill dispenser and a graphic illustration of blood vessels adjacent to the perforated delivery duct.

FIG. 1 is an side cross sectional representation of the tooth medicating apparatus (TMD) 1800 comprising the primary a base section 100, a jacket section 200, and a crown section 300. The crown section 300 houses the mainspring barrel assembly 400, and the tourbillon balance assembly 600. Fitted to the base 100 is one or more surgical implant screws 101 with a perforated delivery duct 102 and is connected to a refillable reservoir 201 shown in FIG. 2 inside the jacket 200. The crown section 300 is fitted with a refill valve 301 which connects via the refill duct 302 to the reservoir 201 passing though the driver pipe 204 as seen in FIG. 2.

Figure 1A:
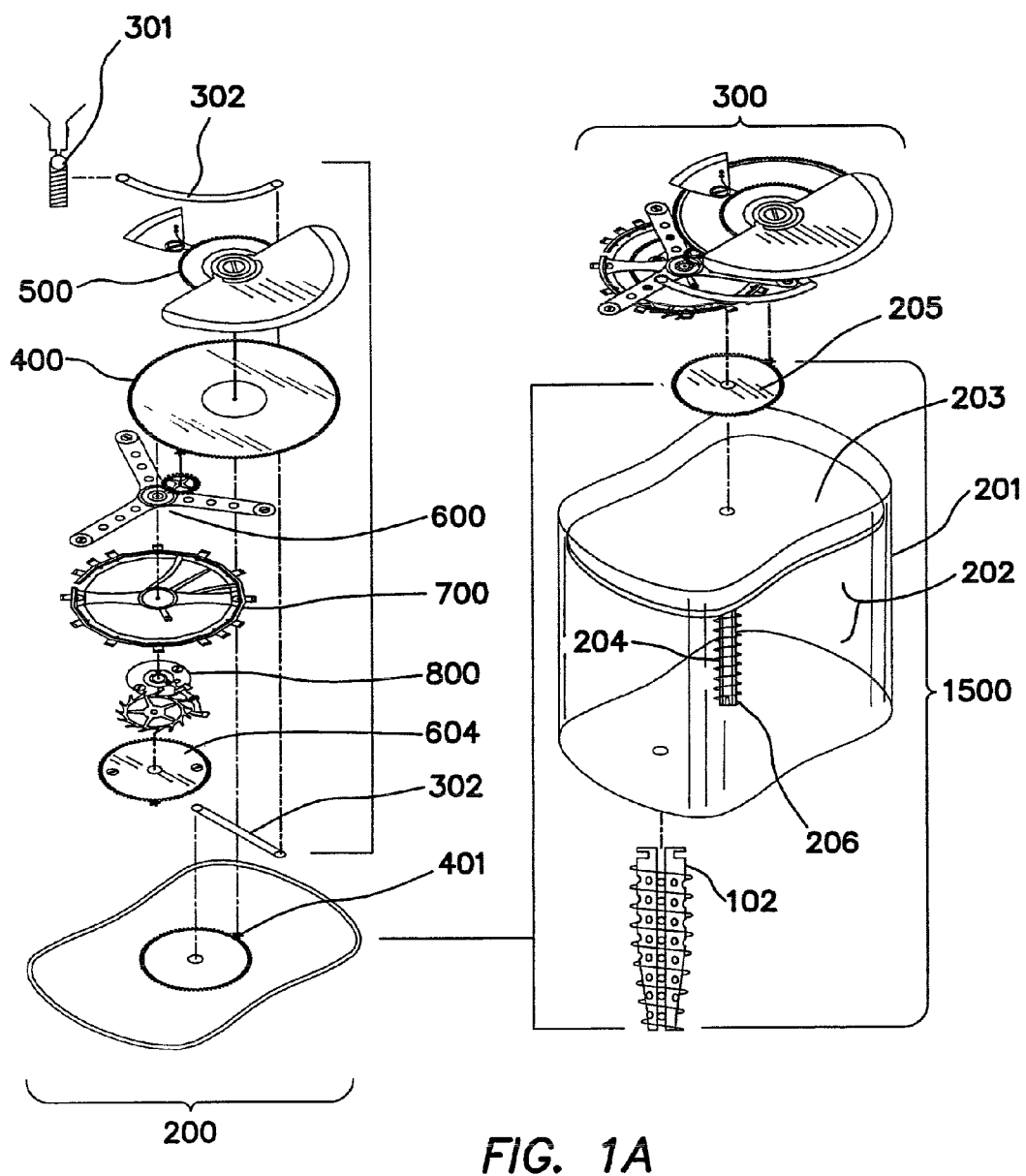
FIG. 1a is an exploded perspective view of the TMD as it depicts the main mechanical components of the apparatus and its spatial layout.

FIG. 1a is an isometric representation of the TMD apparatus 1800 depicting the functional and mechanical arrangement comprising a pump assembly 1500 with a worm-gear arrangement formed by the plunger 203 and driver pipe 204. The energy for driving pump 1500 is obtained from kinetic winder 500 and comprises plunger 203 and driver pipe 204. The movement of worm-gear assembly 203 and 204 generates the pressure differential necessary to drive and deliver the medicating agents and/or fluids 202 via the perforated duct 102.

FIG. 1a further depicts the internal working mechanism of the embodiment. The crown mechanism assembly 300 is shown with its refill valve 301 connected to refill duct 302. The invention further comprises a kinetic winder 500 which stores and converts the energy necessary for driving the TMD pump 1500 comprised of driver pipe 204 and plunger 203. Items 203 and 204 form a worm-gear assembly 1501 in FIG. 4a whose driving energy is obtained from the movement of the jaw bone 50 (shown in FIG. 9) whose energy is transferred to the spring rotor or asymmetric weight 501 (shown in FIG. 3) of the kinetic winder 500. FIG. 1a further depicts the energy from kinetic winder 500 is stored in the main spring barrel 400 which further regulates the energy transfer through the tourbillon assembly 600. This energy transfer is further adjusted by the balance subassembly 700 which releases the necessary amount of energy required to move the plunger 203 onto the driver pipe 204 which results in the drive assembly 1501 in FIG. 4a displacing and compressing the medicating agent and/or fluid 202 through the perforated duct 102. FIGS. 1 and 1a depict that whenever energy is stored in spring barrel 400 the watch mechanism will operate resulting in a constant expression of drug through duct 102 into the bloodstream or tissue of the jaw.

Figure 9:
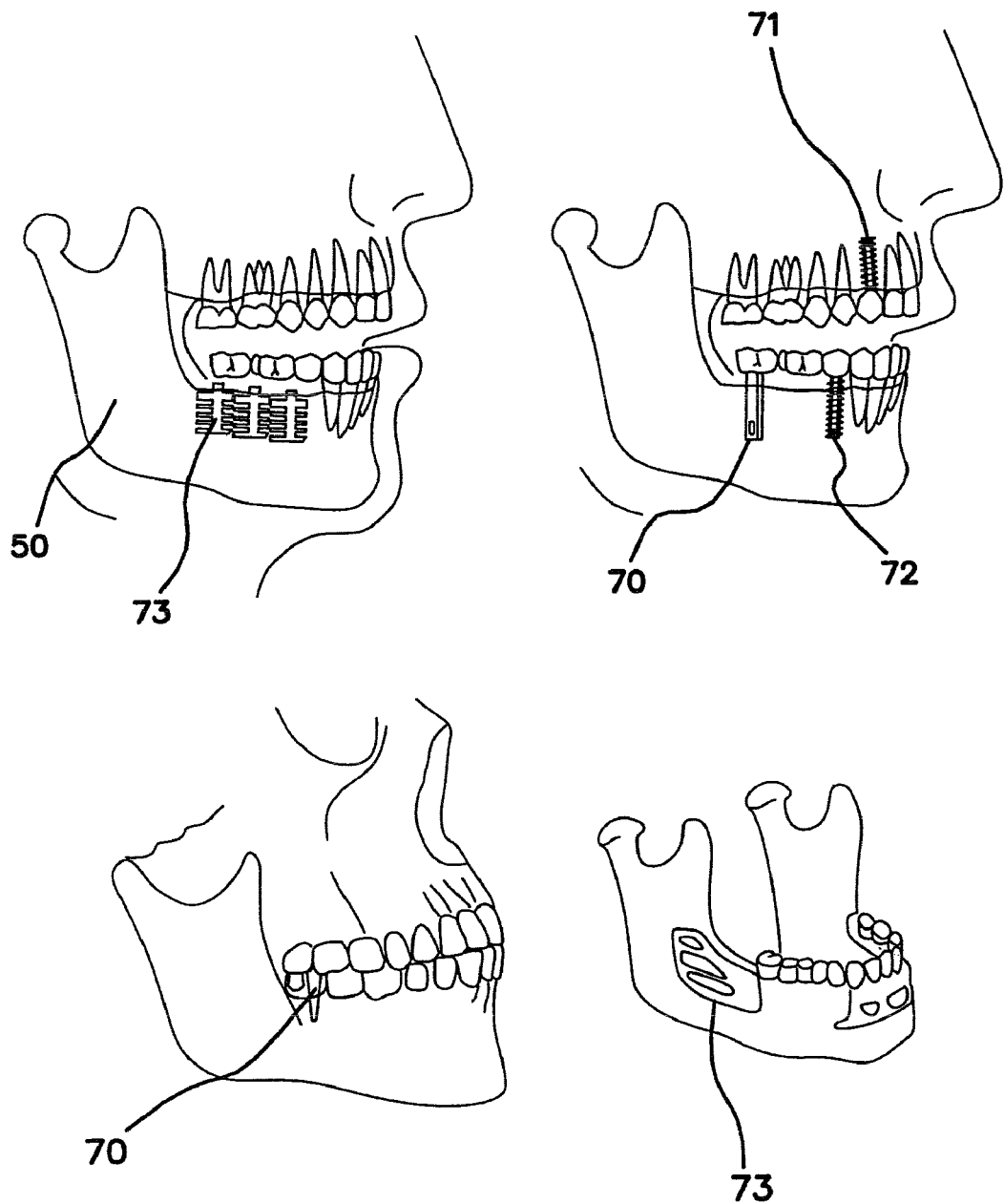
FIG. 9 is a diagrammatic illustration of a molar tooth implant on the lower jawbone, both on the left and the right side of the jaw, as a possible location for implanting the artificial tooth medicating dispenser.

The present invention is further understood in FIG. 1a through the action movement of the drive wheel 205 and the fixed wheel 604 driving the plunger 203 while compressing the chamber 201 so as to cause the medicating agent 202 to be displaced via the perforated duct 102 through the adjacent blood vessels 60 (in FIG. 2) located in the jaw-bone area such as a molar tooth cavity 70 in FIG. 9.

FIG. 2 shows the detail of the reservoir 201 containing medicating agents 202 which are expelled by a plunger 203 as it moves down the threaded driver pipe 204. As the medicating agents are dispensed, they are absorbed into the nearby blood vessels 60 and carried to the brain and other portions of the body. When refilled, the new medicating agents enter the reservoir through the refill spigot 206 at the base of the threaded driver pipe 204.

Figure 2A:
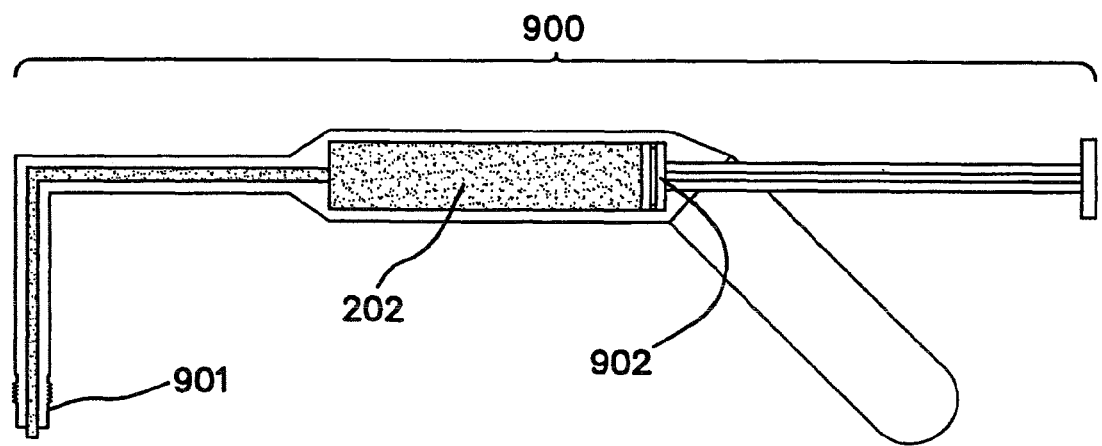
FIG. 2a is a side cross-sectional view of the refill dispenser.

The refilling process of the reservoir 201 is depicted in FIG. 2a. The refill device 900 filled with medicating agent 202 and comprising a refill nozzle 901 and a plunger 902. The plunger 902 forces the medicating agent 202 from the refill nozzle 901 through the refill duct 302 into the reservoir 201 as illustrated by FIG. 2.

Figure 3:
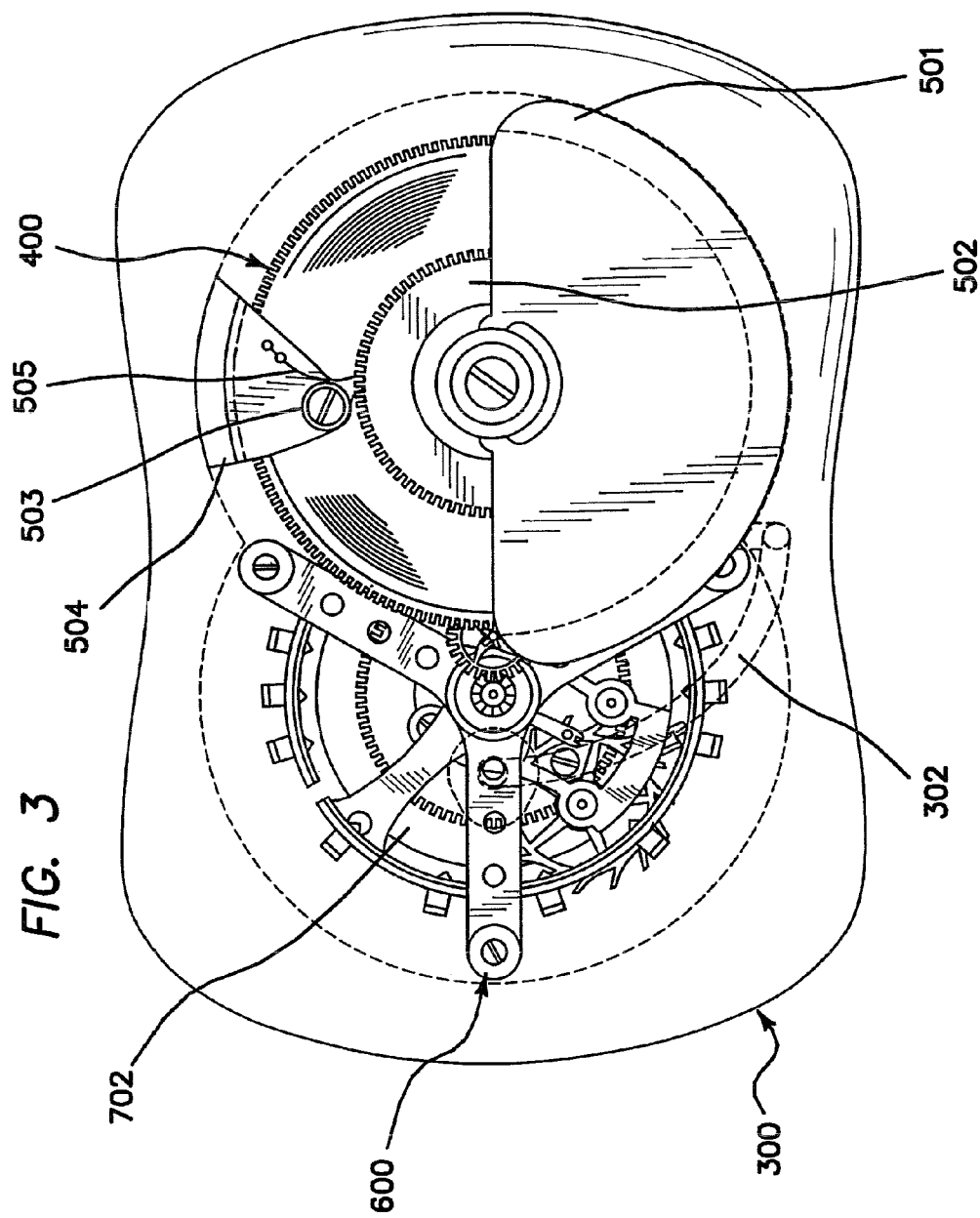
FIG. 3 is a top plan interior view of the crown containing the tourbillon and the kinetic mainspring winder.
Figure 5:
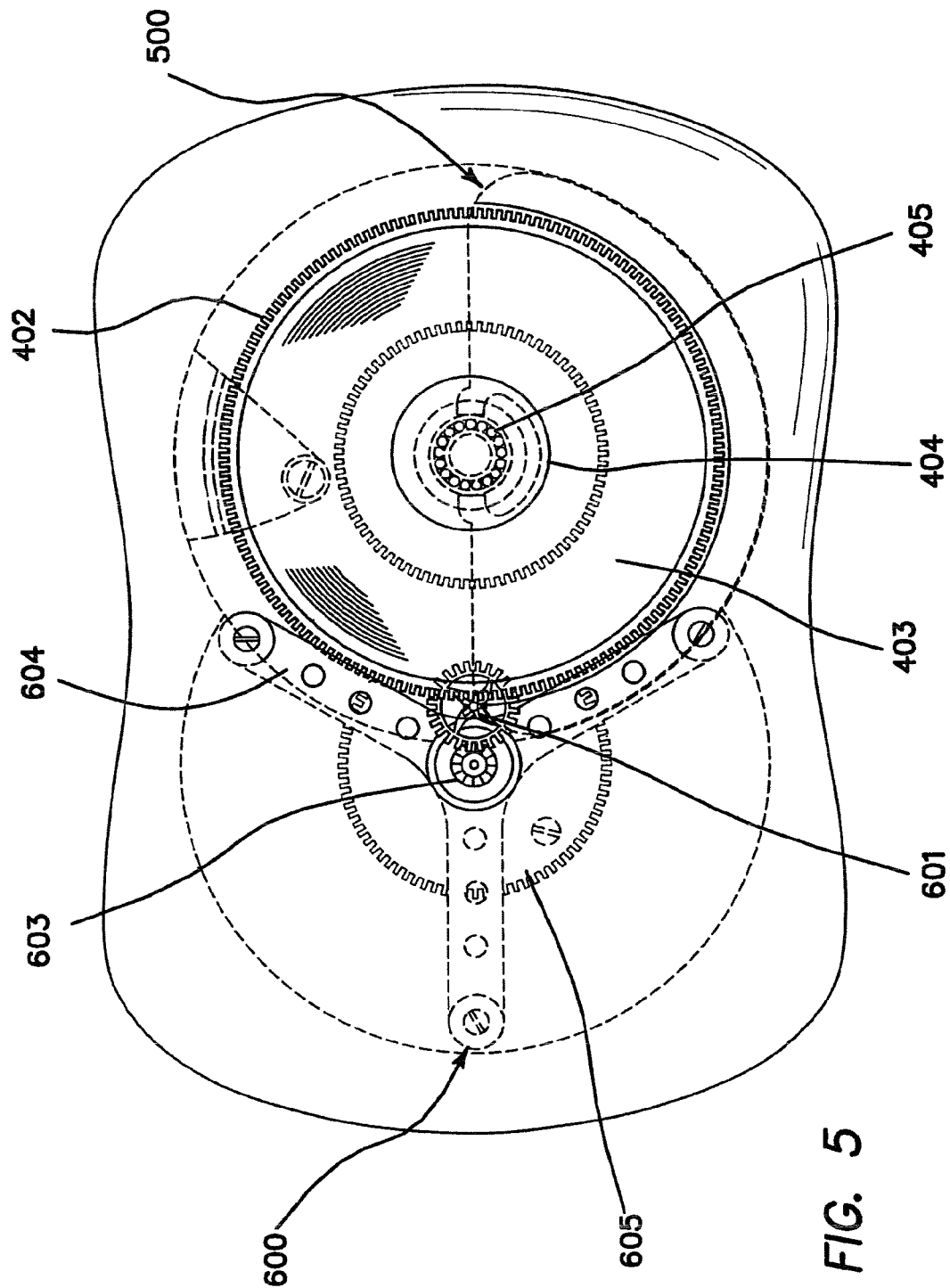
FIG. 5 is a top interior view of the crown and is an orthographic view of the mainspring barrel, barrel wheel, barrel harbor and the ratchet wheel.

FIG. 3 shows a top interior view of the crown 300 and the watch-like mechanism that powers the device including the arrangement of the tourbillon balance assembly 600 with the mainspring barrel 400. The mainspring 403, which is illustrated in FIG. 5, is loaded by the movement of an asymmetrically weighted rotor 501 and mounted to a bearing and wheel 502 and fixed to a ratchet 503 which is caught by a ratchet cock 504 and held by the ratchet spring 505 which is mounted on the ratchet cock 505.

Figures 3A, 3B:
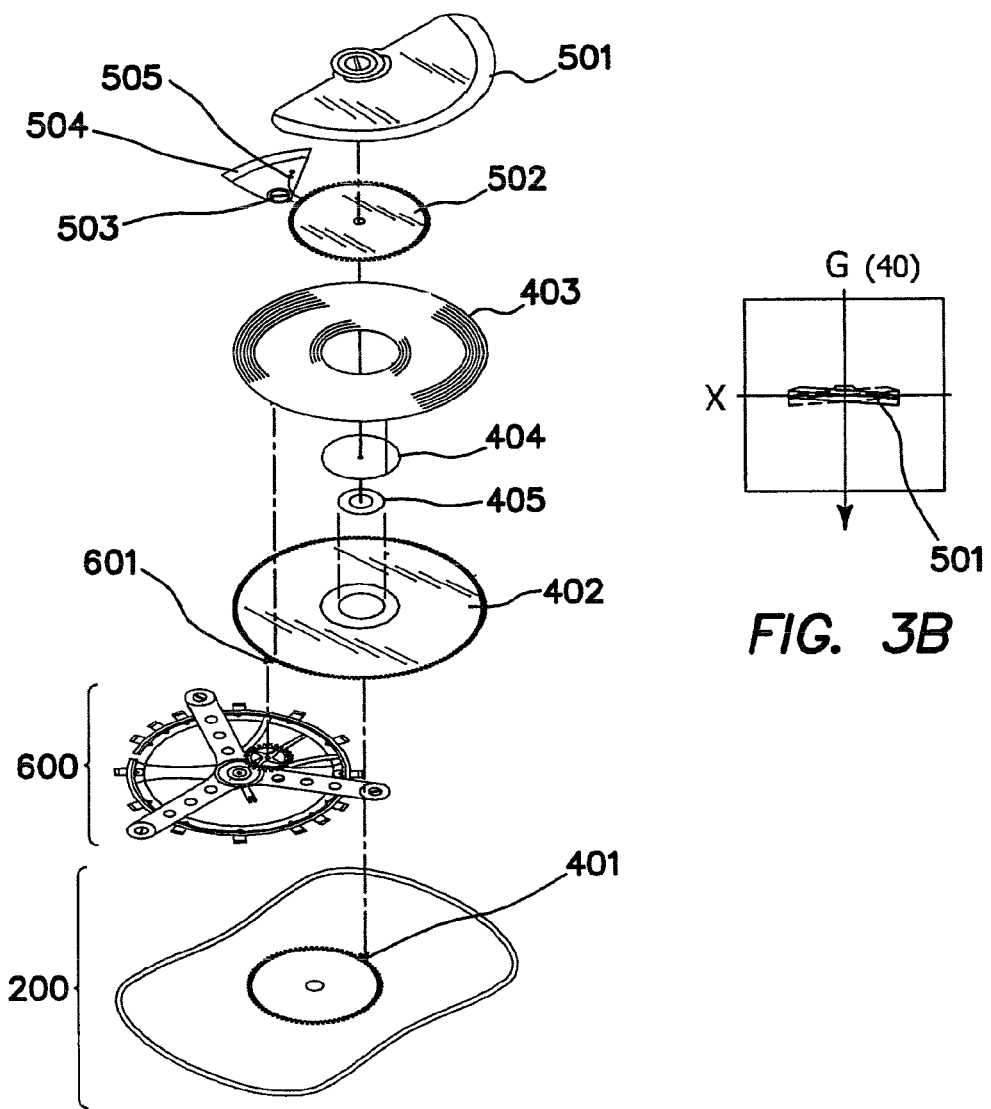
FIG. 3a is an exploded perspective view of the kinetic winder and the mainspring barrel connected to the escapement mechanism and the drive wheel.
FIG. 3b is a diagram depicting the kinetic winder alignment, relative to axis of gravitation.

FIG. 3a is an isometric view of the kinetic winder 500 (FIG. 1a) with its asymmetric rotor 501, ratchet wheel 502, ratchet 503, ratchet cock 504, and ratchet spring 505. The mechanical energy of movement of the jaw bone 50, depicted in FIG. 9, is transferred to the asymmetric rotor 501 due to its dynamic imbalance. Explicitly, the asymmetric rotor 501 transfers energy by engaging the ratchet wheel 502 thereby causing it to move in a unidirectional manner. The ratchet 503, ratchet cock 504, and ratchet spring 505 prevent the cancellation of the action as the asymmetric rotor 501 rotates in the opposite direction.

The use of the kinetic winder 500 in the context of this invention is to provide a continuous generation of energy that is stored in the mainspring barrel 400 by capturing any mechanical energy generated through various movements of the jaw bone 50 due to the asymmetric weight of the rotor 501 relative to the axis of gravity. FIG. 3b depicts the alignment of the asymmetric rotor 501 relative to the TMD implant, which is positioned at a 5 degree inclination from the horizontal jaw plane. Tilting the plane of the rotor 501 with respect to the axis of gravity 40 allows greater generation of energy needed to power the invention by improving the propensity of the rotor 1900 to pick up jawbone 50 movements.

FIG. 3a further depicts the action potential of the rotor 501 relative to the mainspring barrel 400 mentioned in FIG. 1a containing the barrel pinion 401, barrel wheel 402, mainspring 403, barrel arbor 404, and arbor bearing 405. The mainspring barrel 400 drives the mainspring 403 while the barrel arbor 404 rotates with the ratchet wheel 503. FIG. 3a further shows the movement of the barrel 402 which rotates the barrel pinion 401. The barrel pinion 401 meshes with drive wheel 205 thereby engaging barrel pinion 401 in order to rotate the driver pipe 204 while advancing the plunger 203 through the reservoir 201 as previously shown in FIG. 1a.

Figure 4:
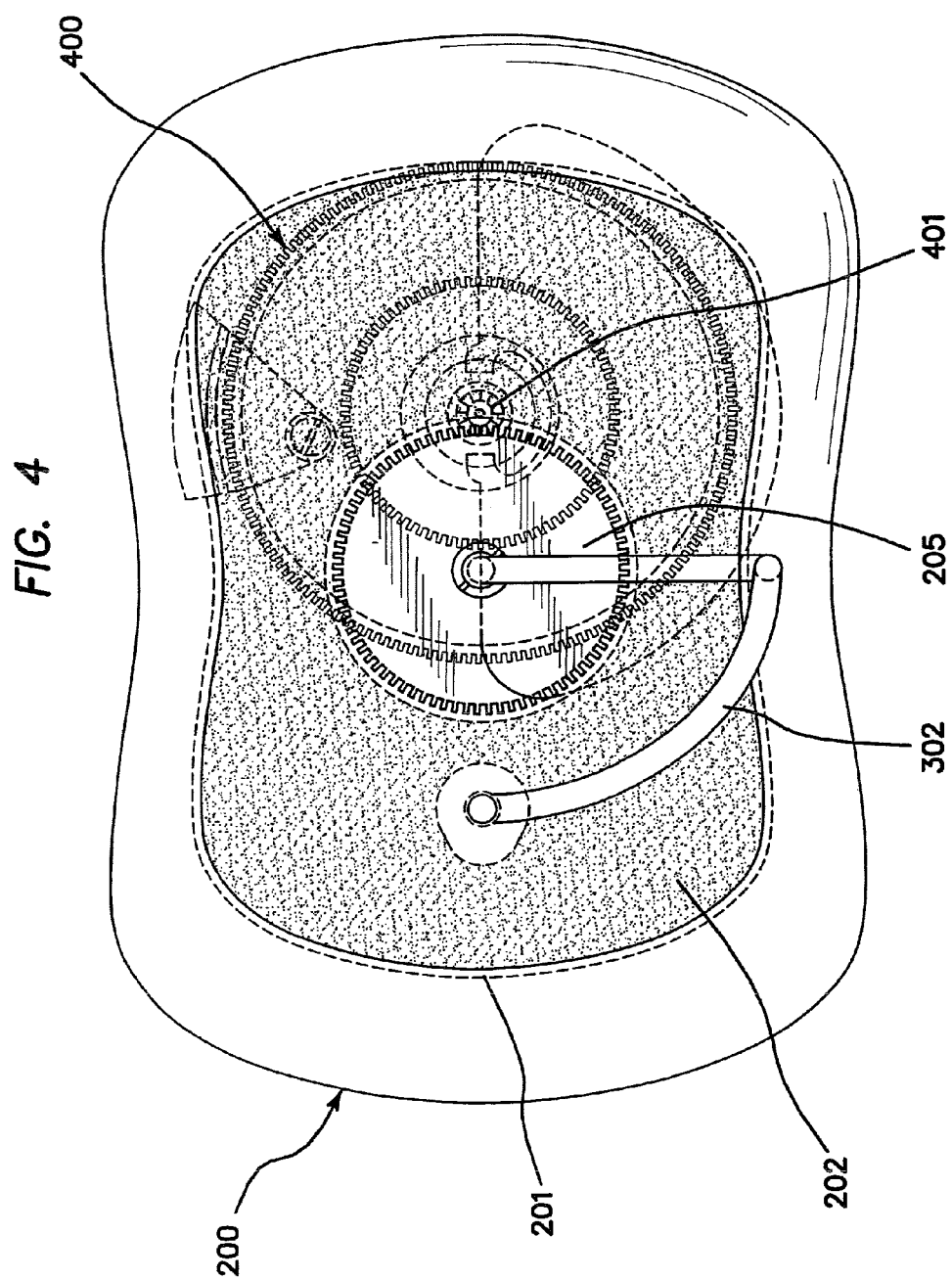
FIG. 4 illustrates a top plan interior view of the crown and the relation between the drive wheel and the barrel pinion, driver pipe and the plunger.

FIG. 4 shows the drive wheel 205 which is engaged by the barrel pinion 401 which moves with the barrel wheel 402 (not shown) in order to rotate the driver pipe 204 and advance the plunger 203 through the reservoir 201 as previously shown in FIG. 1a.

Figure 4A:
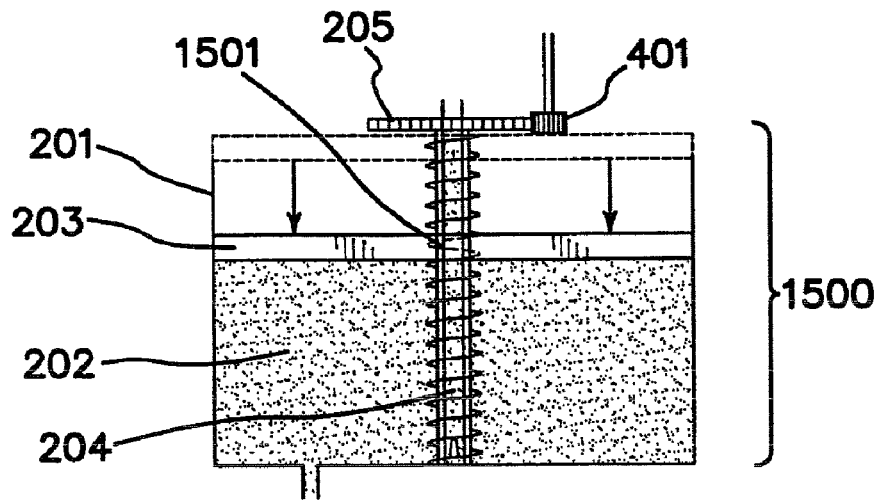
FIG. 4a is a side interior plan view of the pump assembly of the dispenser and the worm gear mechanism.

FIG. 4a shows a side view of the reservoir 201, the plunger 203, the driver pipe 204, and the drive wheel 205 which form pump 1500. Pump 1500 creates the action of the worm gear 101 expelling the medicating agent 202 when driven by the barrel pinion 401. The worm gear movement as described by FIG. 4a can be further modified to include a suitable coil and rectified electrical circuit which would thereby generate the energy necessary to power the CMOS based assembly noted by element 30 as shown in FIGS. 8, 8a, 8b, 8d, and 8e.

FIG. 5 depicts the mainspring barrel 400 comprising a barrel wheel 402 driven by the mainspring barrel 403. The mainspring barrel 403 is fixed at the center to the barrel arbor 404 which rotates with ratchet wheel 503 in FIG. 3a to load the spring.

Figure 6:
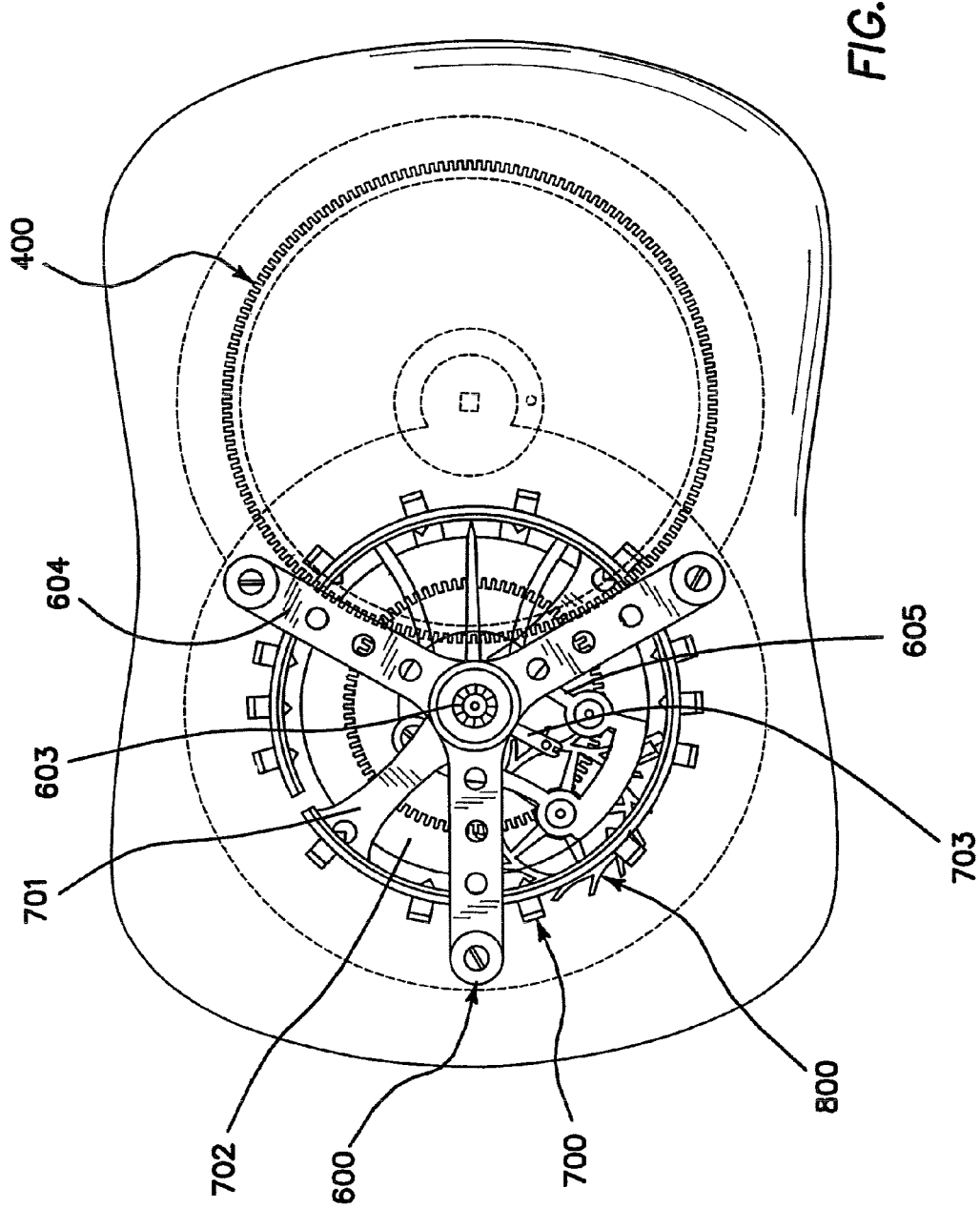
FIG. 6 is a top interior plan view of the crown which graphically represents the escapement mechanism which houses the tourbillon regulating energy-delivery to the plunger.

FIG. 6 shows that the advancement of the mainspring barrel 400 is regulated by an escapement 700 and housed within a tourbillon cage 603 which rotates around a fixed wheel 604. FIG. 5 further shows that on cage 603, a pinion (not shown) engages the barrel wheel 402 via a bridge movement 601. FIG. 6 further depicts balance wheel 701 oscillating by way of a hairspring 702 which is fixed to an adjustable mobile tensing stud 703 causing regular intervals of energy to release from the mainspring 403.

Figure 7:
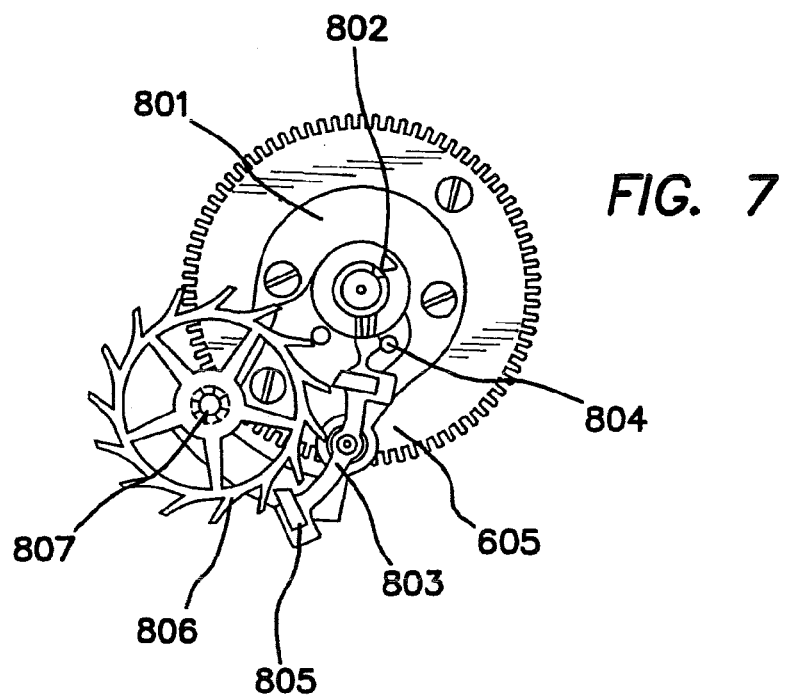
FIG. 7 is a diagrammatic representation of the escape wheel, the pallet fork, the pallet cock and the escape pinion which advances the tourbillon cage.

FIG. 7 shows that the escape wheel 605 depicted in FIG. 6 and pallet fork 803 are mounted to pivots on the pallet cock 801. The roller jewel pin 807 moves with the balance wheel 701 shown in FIG. 6 and kicks the pallet fork 803 between two banking pins 806 which alternately releases and catches the escape wheel 605 with the pallet stones 805 which are held by pallet fork 803. The escape wheel 605 turns the escape pinion 802, which engages the fixed wheel 604 and advances the tourbillon cage 603, the barrel wheel 402, the drive wheel 205, and the plunger 203 expelling the medicating agent 202 as shown in FIGS. 4a, 5, and 6.

Finally, FIG. 9 illustrates the implanting of the TMD in the space of a molar tooth or alternatively in the location of a previously removed wisdom tooth. The entire assembly disclosed above is contained within the artificial tooth which comprises a base 100, a jacket 200, a crown, 300 and an implant post 102 made of titanium as depicted in FIG. 1. The metal anchor 102 acts as a substitute for wisdom tooth implant 74. The device is surgically implanted into the jawbone 50. The bone bonds with the titanium post 102 thereby creating a strong foundation for an artificial tooth within the blood vessel 60 surrounding the jaw-bone 50 as illustrated by FIG. 2. Small posts are then attached to the implant which protrudes through the gums. These posts provide stable anchors. The above disclosed device is customarily implanted by an orthodontic surgeon.

Many patients fail to respond to treatment due to the lack of efficacy or the production of side-effects which leads to patient non-compliance with the medicating regimen. The invention as disclosed above can be used to improve the art of dispensing medicating agents for many cases. For example, patients who suffer from acute manic episodes may use the present apparatus as a form of pharmacological therapy and use any number of typical anti-psychotic drugs as a maintenance program including lithium, valporate, and carbomaezine.

Another use of the apparatus is to specifically improve the treatment of bipolar affective disorders because as clinical evidence suggests, medicating agents such as lamotrigine (LTG) have shown a broad spectrum of utility by inhibiting neural hyper excitability and modifying synaptic plasticity via usage of a voltage (−) dependent inhibitor of neuronal voltage activated $Na^+$ channels and possibly $Ca^{++}$. For example, Protein Kinase C (PKC) concentrations play a significant role in the pathophysiology of bipolar disorders. The effect of lithium and its concentration tend to attenuate the PKC function and thus the use of the pump and its associated watch-like mechanism of the claimed invention improve the ability to regulate and medicate the patient in such processes. Clinical observations indicate that the signal transduction mechanisms in bipolar disorders are associated with intercellular calcium homeostasis. The claimed invention can release the medicating agent in correct proportion to the PKC concentration and the watch-like mechanism of the claimed invention enables one to accurately and timely release the medicating agents thereby obtaining a effective mechanism for such treatments.

The current invention will also enable drug manufacturers to evaluate the effectiveness of its drugs during animal and clinical studies because of details provided from the local delivery from the tooth medicating apparatus, specifically the absorption, distribution, and elimination of a tested drug in a local setting. Other characteristics such as dose, cycle, circadian time effects, and the entire pharmacokinetic as well as pharmacodynamic behavior of the medicating agents can be evaluated employing the TMD apparatus because of its local delivery and ability to provide controlled dispensation associated with its watch-like mechanism.

Figure 2B:
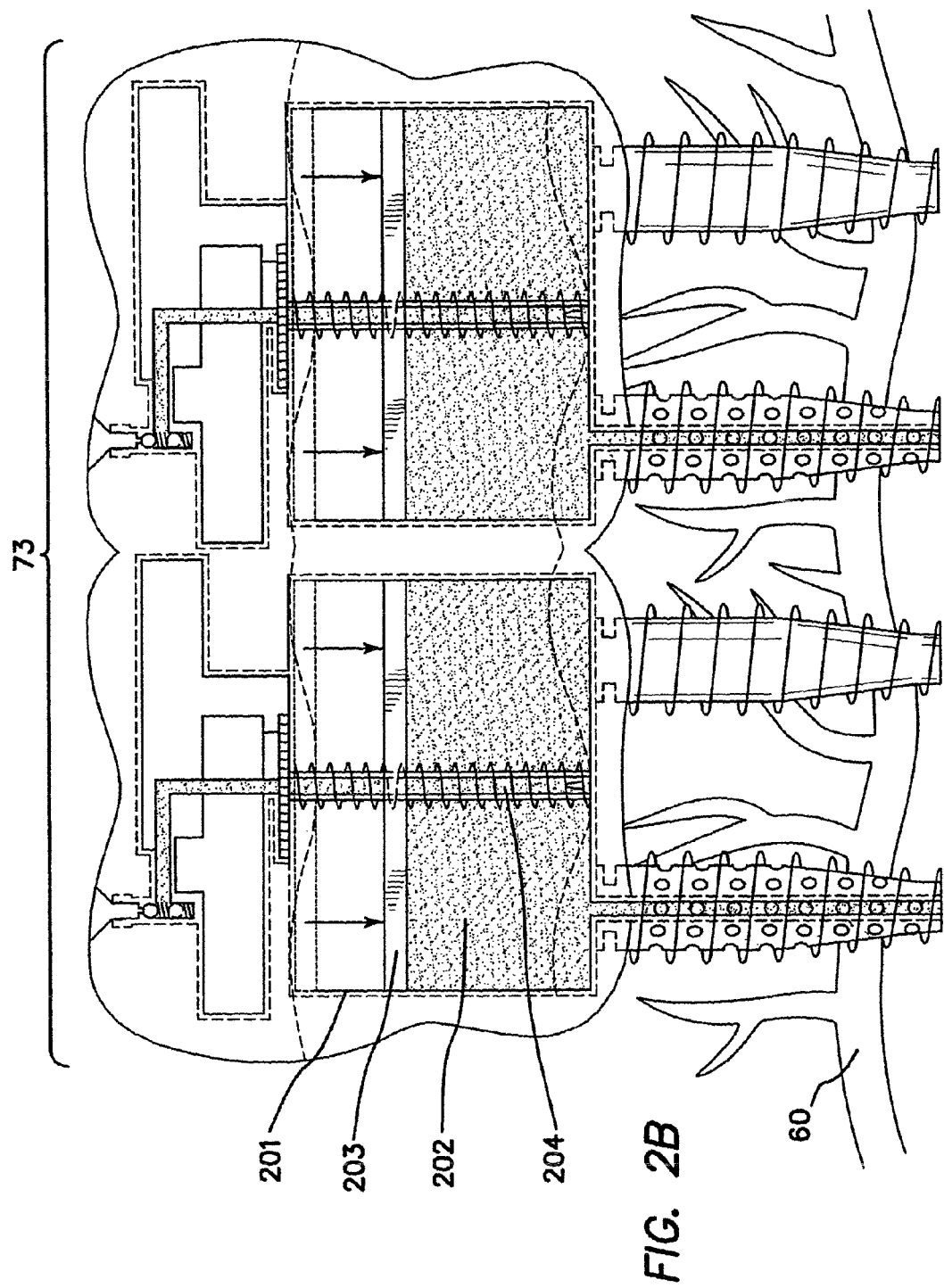
FIG. 2b is a side cross sectional view of the invention with two chambers used in an orthodontic bridge implant configuration.

In another embodiment of the invention, the apparatus is used in a poly-pharmacy regimen when more than one medicating agent is required. FIG. 2b illustrates an orthodontic bridge 73 which incorporates two containers 201 so as to afford a poly-pharmacy approach. The reservoir 201 containing medicating agents 202 which are expelled by a plunger 203 as it moves down the threaded driver pipe 204. As the medicating agents are dispensed, they are absorbed into the nearby blood vessels 60 and carried to the brain and other portions of the body. When refilled, the new medicating agents enter the reservoir through the refill spigot 206 at the base of the threaded driver pipe 204 as previously disclose above.

FIG. 9 also further illustrates a TMD implant in the location of molar tooth cavities 70, 71 and 72 in the side of the jaw. The apparatus is shown in FIG. 9 at tooth number 32 (3rd molar). Similarly, FIG. 9 depicts a possible arrangement of a comprehensive bridge 73 implanted at the lower teeth of jawbone 50. The apparatus is an integral part of the bridge while reservoir 201 (shown in FIG. 2) is expanded to include larger or multiple chambers for use in cases where a polypharmacy regiment is required.

This particular embodiment of the invention the apparatus provides a controlled mechanism for cases where polypharmacy is essential in treating patient-resistant euphoric mania (characterized by elevated mood, hyperactivity, rapid speech, refractory to standard treatments and anticonvulsants). The use of a polypharmacy approach shows dramatic improvements in symptoms and with the aid of the apparatus, the regulating of multiple medicating agents (polypharmacy) will be more obvious and intuitive. For example, when dealing with a bipolar illness, treatment by single agents is not always effective. Supplemental anti-depressants, anti-manic, antipsychotic, or hypnotic medicating agents must sometimes be used. However, these traditional adjunctive medications are associated with potential problems such as mania, accelerated neuroleptics, dyskinesia, etc. The use of the apparatus and the method presented allows a combination of therapies to be controlled, tailored, and regulated by the patient's specific pharmacokinetic and pharmacodynamic attributes.

Figure 4B:
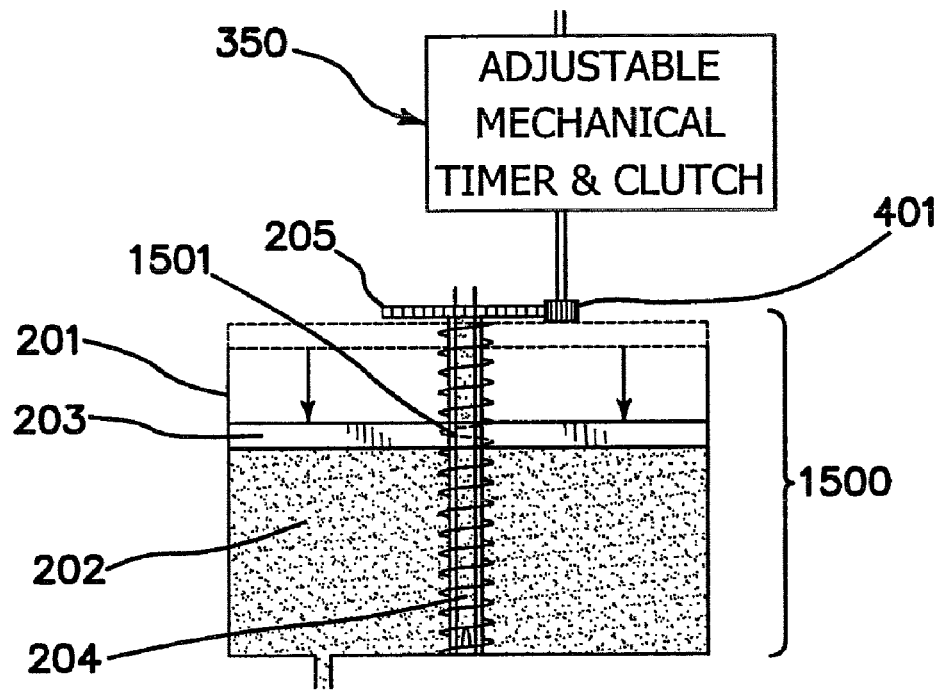
FIG. 4b is a side interior plan view of the pump assembly of the dispenser and the worm gear mechanism and adjustable timer modified with a clutch assembly for control of time release schedule.

In yet another embodiment of the invention, the apparatus is configured to provide the user with an "on demand" option for dispensing the medicating agents. FIG. 4b is a side interior plan view of reservoir 201 depicting an alternate drive configuration which comprises a user-adjustable mechanical timer and clutch assembly 350. The adjustable mechanical timer and clutch assembly 350 is analogous to the principle behind an alarm clock timer, which is clear to those familiar in the art, and is capable of adjusting the amount of medicating agent 202 to be dispensed based on prescribed mechanical settings. The adjustable timer and clutch assembly 350 diverts the transfer of energy from the barrel wheel 402 to the barrel pinion 401 and then to a mechanical timer (not shown) which triggers the clutch to engage the barrel pinion 401 only for the duration of the timed release. The mechanical timer and clutch assembly 350 may be mechanically controlled by conventional adjustments (not shown) manipulated by the physician or may be electronically controlled through conventional software control of conventional electromechanical timers.

This particular embodiment of the invention allows dispensation of the medicating agents with the use of an "on demand" feature via the use of "timers" or "triggers". This is especially helpful when used to correct and provide effective implementation of medicating agents for conditions such erectile dysfunctions due to the ability of the apparatus to provide an on-demand option for the release of medicating agents to the patient's body. For example, in order for medicating agents such as Viagra to correct erectile dysfunction (ED), they need to inhibit phosphadiesterase Type 5 (PDE5) which is a specific marker and requires a timed release based on user decision, specifically to erect the target penis. However use of the claimed invention can better achieve this result and make it more intuitive and obvious because the patient can select any specific time to dispense the medicating agent.

Figure 8:
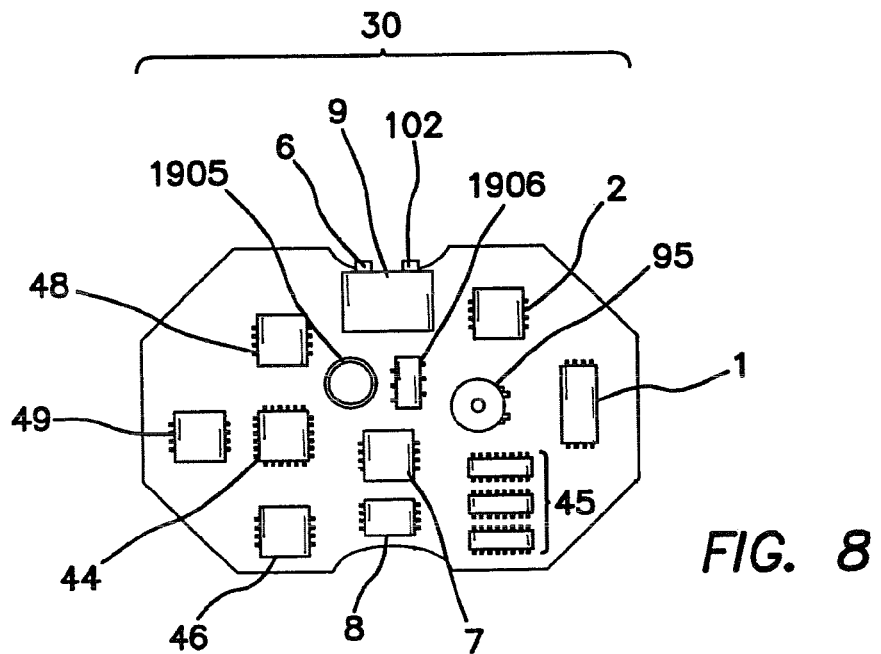
FIG. 8 is an plan view of the layout of a printed circuit board (PCB) module assembly containing the sensor and microcontroller used in another embodiment of the TMD which is an optional architecture incorporating sensor (s) and electronic assembly.

In yet another embodiment of the invention, the apparatus contains a device known as an electronic regulator 30 as illustrated in FIG. 8. This device enables one to sense, control, regulate, and dispense medicating agents into a patient's jaw bone 50 shown in FIG. 9. The electronic regulator 30 further contains a free ion sensor 9 which detects minute changes (elevation) in $Ca^{++}$ concentration. The output of the free ion sensor 9 is coupled to the input of an instrumentation amplifier 8 and amplifies the signal from the free ion detector 9 as shown in the schematic of FIG. 8d. The amplification rate is a function of resistor value. The output signal from the amplifier 8 is fed to the input of an analog to digital converter (ADC) 7. After determining the value of free ion concentration from the use of a lookup table residing in a ROM (read only memory), RAM (random access memory), or NVM (nonvolatile memory) microchip 45 coupled to ADC 7, it is transmitted via the ADC 7 to a microcontroller 1. The pump 1500 with its worm gear 1501 is activated (as shown in FIG. 4a and/or optional configuration as noted by FIG. 4b) to deliver the medicating agent 202 via the perforated duct 102 as further described by FIG. 8b.

Figure 8A:
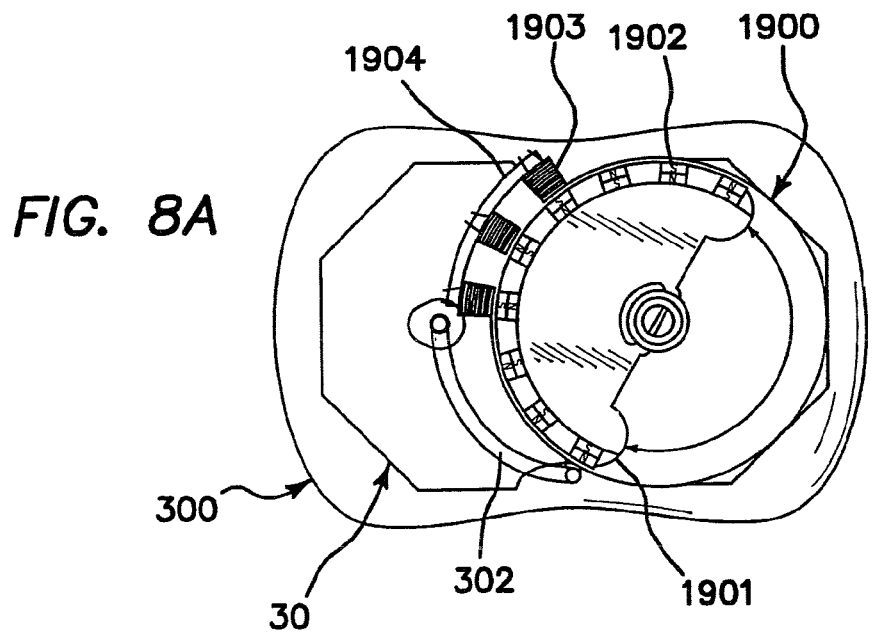
FIG. 8a is a top plan view of the Faraday pendulum generator and a modified asymmetric weighted rotor in the embodiment using the PCB of FIG. 8.

FIGS. 8 and 8a also depict the relative location of the electronic assembly forming the regulator which controls the dispensation of the medicating agent from the apparatus. FIG. 8 further depicts the necessary building blocks to configure the electronic regulator 30 with a plurality of sensor elements such as a free ion detector 9, a pulse rate sensor 48, blood chemistry analyzer 49, body temperature sensor 46, a multiplexer 44, a microcontroller 1, an op amp 8, a DAC 2, and a ADC 7, a capacitor 1905, a rectifier circuit 1906, and an electric motor 95. The above noted building blocks that form electronic regulator assembly 30 can be easily ascertained by those who are familiar with the art.

Figure 8B:
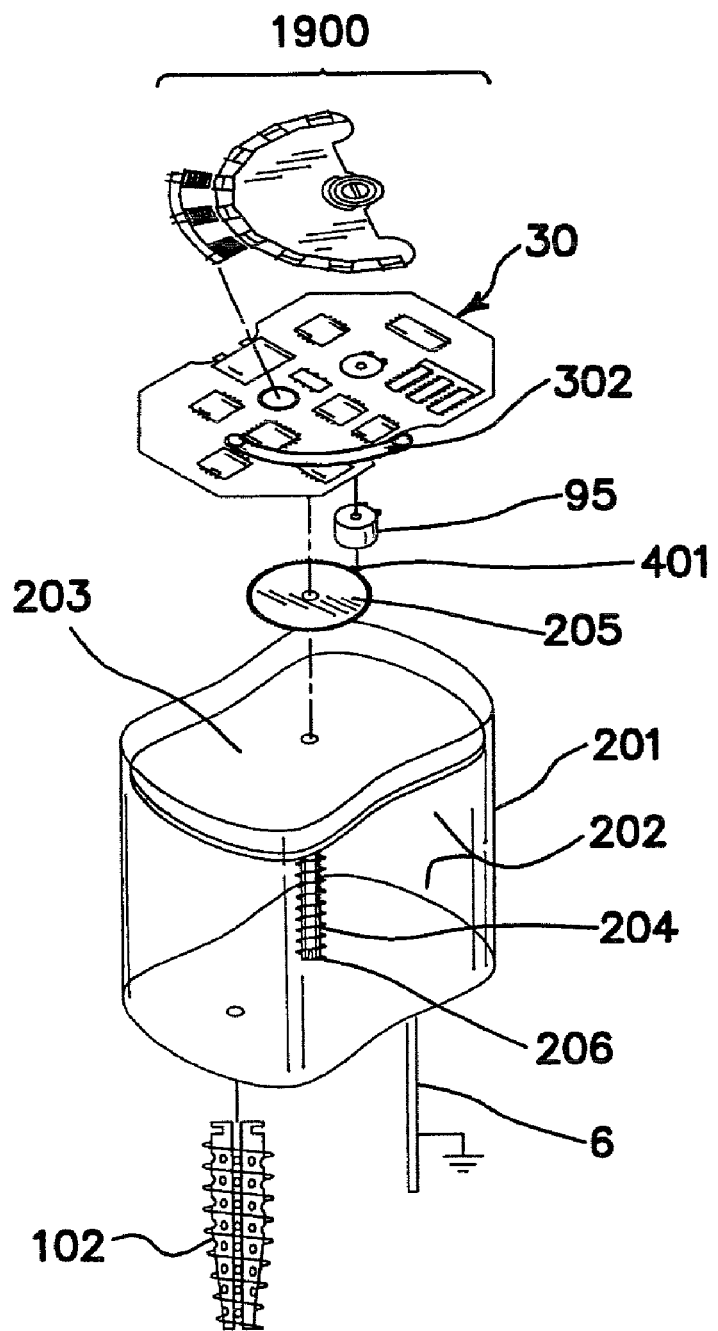
FIG. 8b is an exploded perspective view of the medicating agent dispensing apparatus of FIGS. 8 and 8a, showing the three major parts of the device; the Faraday generator, the electronics module, and the dispensing container.
Figure 8C:
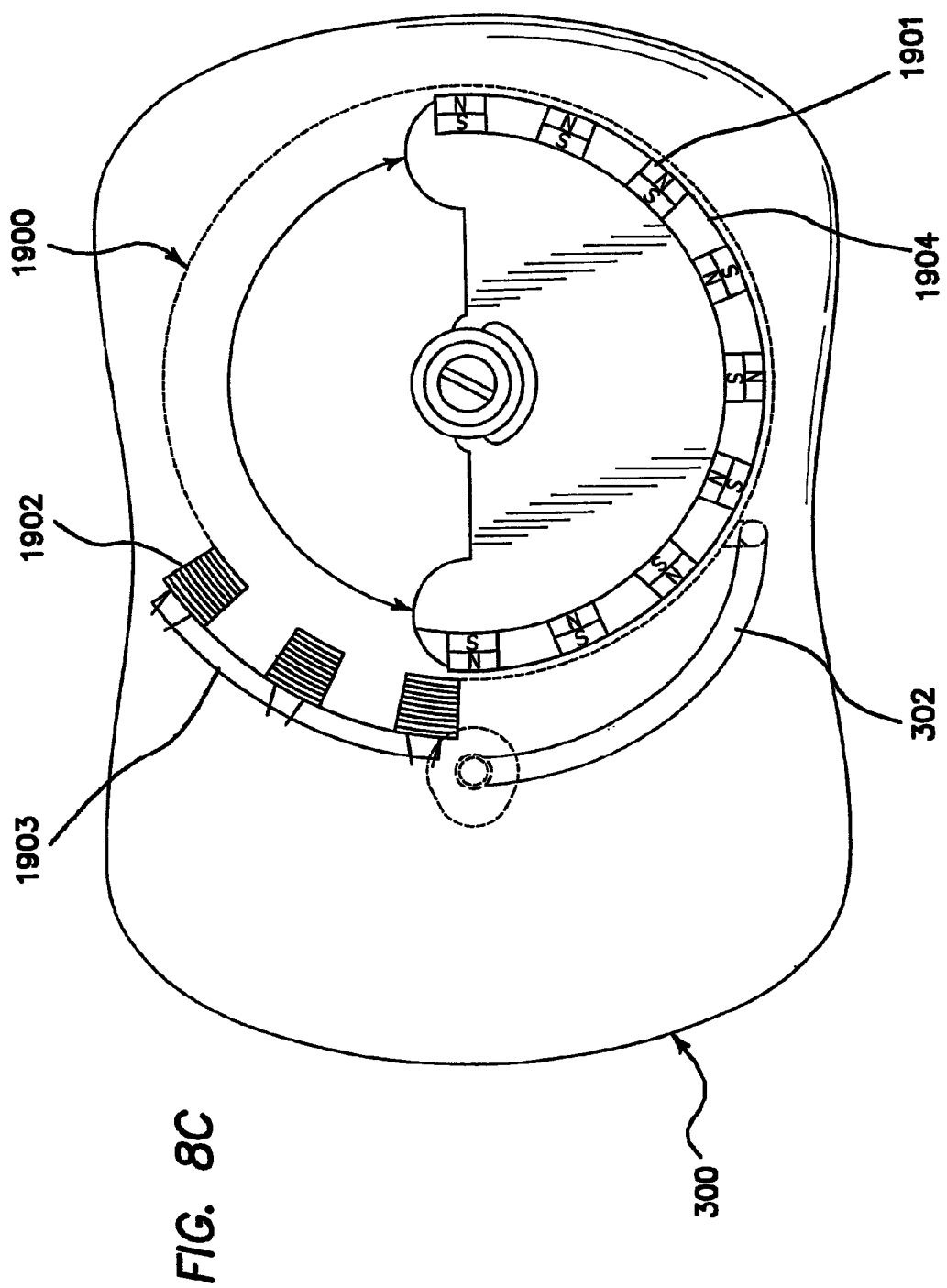
FIG. 8c is a top diagrammatic view of the Faraday generator with its E-frame coil assembly and the associated integrated magnetic element of the asymmetric weight rotor.
Figure 8D:
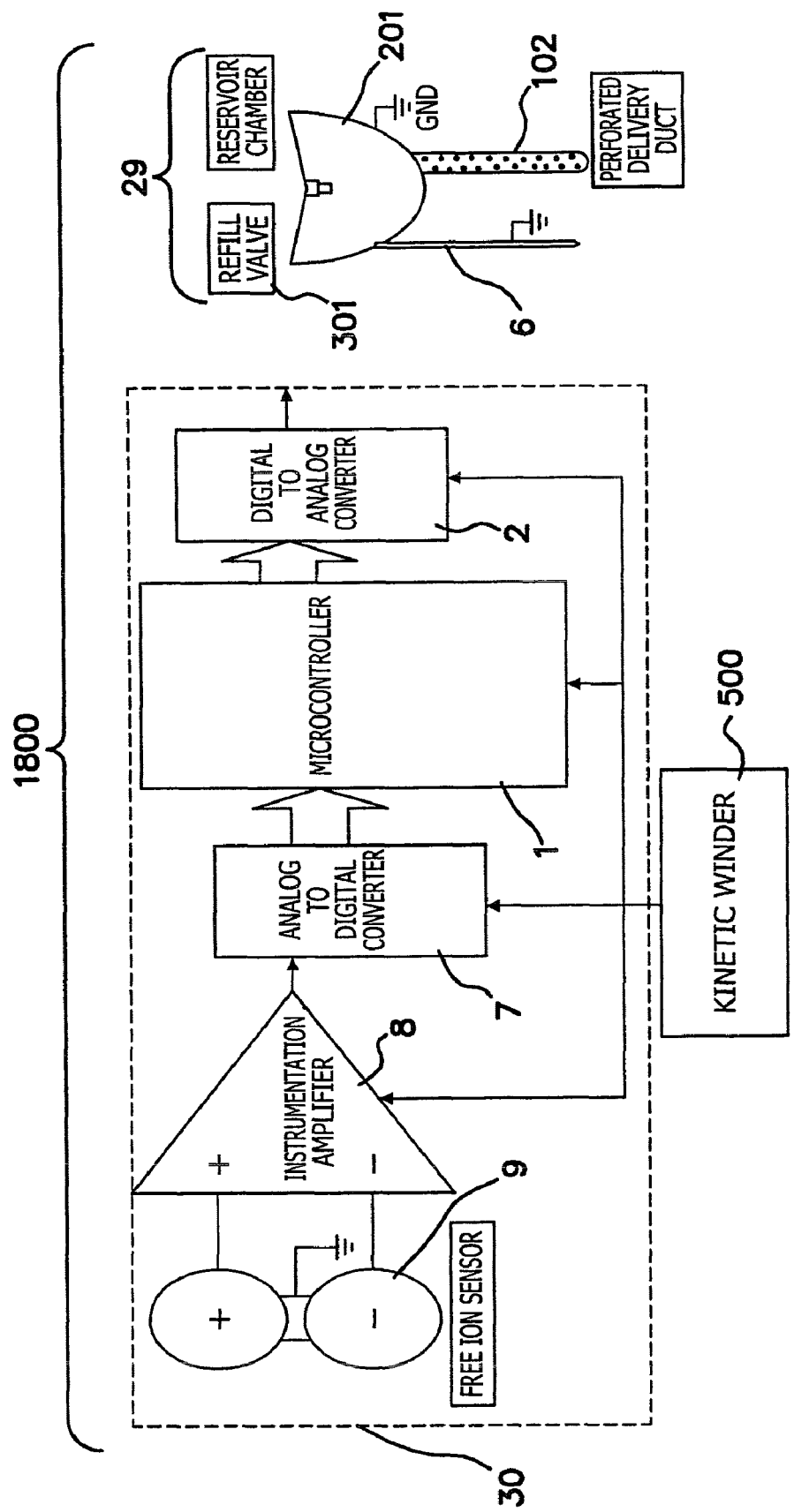
FIG. 8d is in the left hand portion a block diagram of the embodiment of the TMD having multiple sensors and in the right hand portion a diagram of the physical components of the TMD. The sensors can vary and be of a general type such as for temperature measurement, or specific such as pulse rate sensor or a $C_a^{++}$ free ions detector.
Figure 8E:
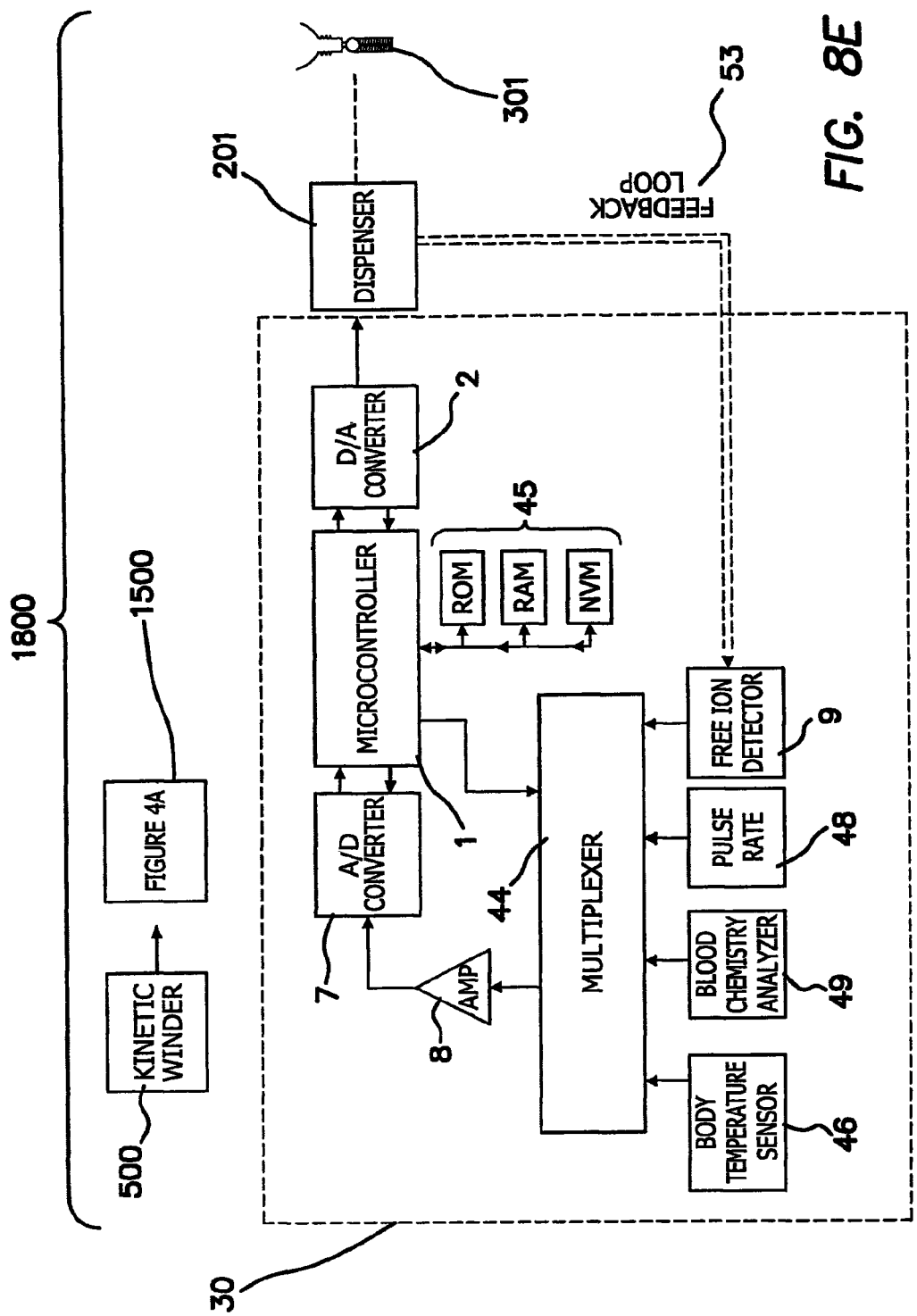
FIG. 8e is a schematic diagram of the TMD depicting the sensor and the servo closed loop architecture.

FIGS. 8d and 8e are block diagrams which illustrate the general outline of the electronic regulator. The block diagram of FIG. 8e illustrates the relationship between the sensing leg (e.g. elements 9, 46, 48, and 49) and the microcontroller 1 to enable the TMD apparatus to regulate the dispensation of the medicating agent 202 while employing a worm gear 1501 and the pump action 1500 as described above.

FIGS. 8d and 8e further detail the preferred embodiment shown by FIGS. 8, 8a, 8b, 8c, 8d, and 8e whereby an array of sensors, such the pulse sensor 48, temperature sensor 46, free ion sensor 9, and a blood chemistry analyzer 49 are incorporate multiplexer 44, which allows the microcontroller 1 to sample the various sensors at a sampling rate defined by the program residing in the microcontroller 1. The multiplexer used in this case is the Motorola PIC12LC672 and its function is well known in the art.

Finally, the schematic depicted in FIG. 8e illustrates that the sensors such as the pulse sensor 48 are coupled to the multiplexer 44. The pulse sensor 48 is a miniature electronic condenser microphone that sends a signal to the input of the multiplexer 44. The multiplexer 44 then sends the signal out to the amplifier 8 which amplifies the signal and feeds it to the A-to-D converter 7 which is a part of the microcontroller 1. Microcontroller 1, part number PIC12LC672, has an A-to-D converter 7 and either a ROM, RAM, or NVM microchip 45 or combination thereof built in. Once the signal from the pulse rate sensor 48 senses the pulse rate from within the jaw 50, it is sent to the microcontroller 1 which analyzes the data and stores them for retrieval. Due to the pulse rate background noise, a Fast Fourier Transform (FFT) can be used as part of ROM 45. The electrical power to operate all the electronics is obtained from the kinetic winder 1900.

In yet another embodiment of the invention, the apparatus uses the energy from the mechanical movement of the jaw bone to power a Faraday generator which in turn then provides electric power to the device. It is to be expressly understood that the following explanation of the physical principles involved in the invention are not to be limiting in any way on the claims. All of the scientific explanations and descriptions presented below are meant to be illustrative only and are provided in order to help better understand the invention and what is being claimed as a whole.

A simplified description of the minimal geometry required in generating the necessary EMF used in the invention is noted by the Faraday-Maxwell Induction Rule:

$$\varepsilon = -N \frac{d\Phi_B}{dt},$$

where $\varepsilon$ is the electromotive force (emf in volts, N is the number of turns of wire, and $\Phi_B$ is the magnetic flux in webers through a single loop. More generally, the relation between the rate of change of the magnetic flux through a surface S enclosed by a contour C (see FIG. 8c for spatial layout of the "contour C" which can be numerically parameterized by calculating the coil 1902 size relative to the frequency of rotation of the asymmetric weight rotor 1900 with its integrated set of magnets 1901). Rendering the invention its metric value so as to generate the necessary energy to power the electronic module 30, we further calculate the electric field along the "contour C" by the use of Faraday's law of induction as:

$$\oint_C E \cdot dl = -\frac{d}{dt} \int_S B \cdot dA.$$

In this equation E is the electrical field, dl is an infinitesimal element of the contour C, and B is the magnetic field.

Figure 8F:
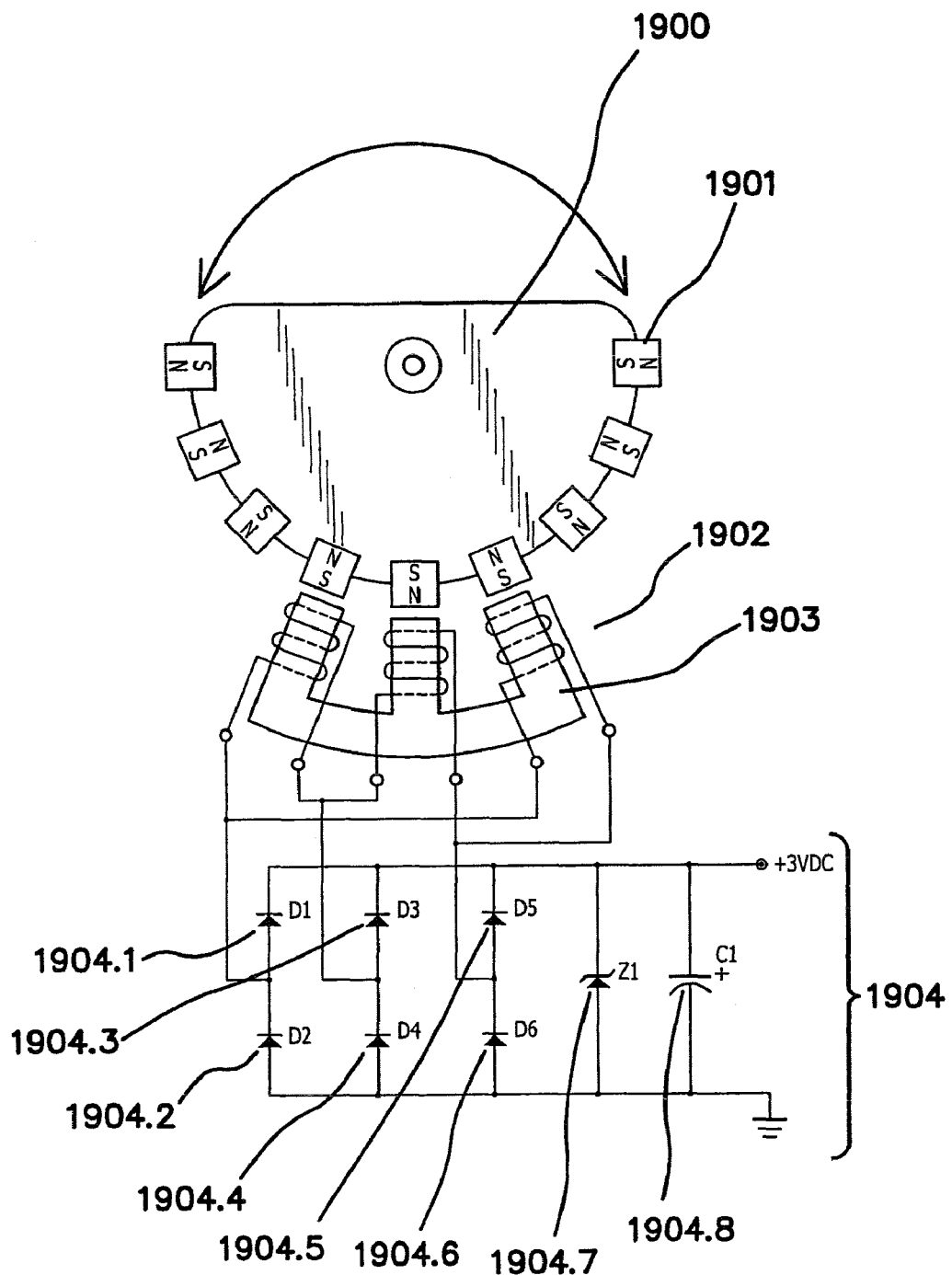
FIG. 8f is a schematic diagram of the Faraday generator with its pendulum topology, storage capacitor and a rectifier circuit.

The schematic in FIG. 8f depicts the use of a modified Faraday generator using a pendulum mechanism 1900. The Faraday principle is employed to create rapid flux changes across a coil 1902. The optimal topology for this principle is the use of a pendulum mechanism which swings on its axis of rotation 40 due to the jaw bone movement 50. Alternating polarity NdFeB magnets 1901 on the edge of the pendulum enable a rapidly changing magnetic flux. By employing the Faraday induction principle we can calculate and predict the effect of the pendulum 1900 oscillation with reference to the coil 1902 size and the ferrite core 1903.

The volume and space allotted for the TMD apparatus requires a reduction in size of a super capacitor C1 1904.8 such as a Sieko XH-HG ultra capacitor as depicted in FIG. 8f. It is important to provide a good source of averaged pulsed power and this task is achieved by using a three phase coil assembly 1902 mounted on the E frame 1903. The coils 1902 are wound onto an E shaped curved ferrite core 1903. The pendulum 1900 swings the magnets across the pole faces of the E core and thus alternates the flux through them. The coils are inductively induced with voltage. The rising voltages across the coils are then converted into direct current by a DC rectifier and energy storage system 1904. The three phase diode bridge rectifier is comprised of six diodes: D1 1904.1, D2 1904.2, D3 1904.3, D4 1904.4, D5 1904.5, and D6 1904.6. The rectifier diodes are clamped by a low leakage zener diode Z1 1904.7 which clamps the voltage to 3V. The voltage appearing across Z1 1904.7 is also seen across C1 1904.8. The capacitor is charged by the rectified current of the bridge rectifier 1904. The power supply shown in FIG. 8f can provide a steady source of voltage to the CMOS microprocessor 1 mounted on circuits 30.

FIG. 8a depicts the Faraday pendulum assembly 1900, the rotor 1901, and inserted magnets 1902 aligned with coil 1903 and wrapped on the frame 1904. FIG. 8b is an exploded perspective view of the connection of Faraday assembly 1900 to the capacitor 1905 (FIG. 8) on the PCB 30, and the electric motor 95 which drives the barrel pinion 401. The above noted architecture provides for the incorporation of a servo closed loop modality 53 (see FIG. 8e) so as to enable the TMD apparatus 1800, to modify its medicating agent(s) 202 rate of dispensation and further regulating the rate of absorption, distribution, and elimination relative to the multiple parametric mechanisms of drug intake based on patient-specific conditions as previously defined by the microcontroller 1 and the look-up tables residing in the RAM, ROM, or NVM microchip 45.

Techniques of employing magnets in order to control and stabilize the pendulum are described in U.S. Pat. No. 4,723,233 to Beebe, U.S. Pat. No. 3,885,753 to Connor, U.S. Pat. No. 3,100,278 to Reich, and U.S. Pat. No. 7,306,364 to Born et al. are incorporated herein by reference. The above mentioned patents teach that the use of a pendulum in conjunction with permanent magnets or electromagnets for the purpose of adjusting and stabilizing the pendulum to keep an accurate time. All the above patents disclose a mechanism by which the pendulum is controlled by fixed magnets so that the pendulum oscillations and unexpected deviations in space and or in time are corrected by a magnetic force. The use of a Faraday pendulum generator in this embodiment is related to the ability of the asymmetric rotor 1900 to harness the kinetic energy generated by a jawbone movement 50, to "translate" the energy of the natural displacement of the jawbone 50 to drive the movements of the asymmetric rotor 1900, and thence to generate electrical power from the relative motion of the magnets and the coils in the Faraday generator.

The above action is used to generate the necessary energy to power the command and control circuitry of motor 95 in FIG. 8b to dispense the medicating agents 202. The resultant EMF generated from the Faraday pendulum 1900 (and its associated circuit 1904 and capacitor 1904.8 in FIG. 8f) thereby enables the transfer of energy to an electric motor 95 that drives the barrel pinion 401 and the plunger 203 by the use of a worm gear mechanism 1501 to create a pumping action. The resulting displacement of the medicating agent 202 is further controlled by a servo closed loop 53 schema noted in FIG. 8e which regulates (by modifying or amplifying) the delivery of the medicating agent 202. This action is regulated by the by the conventional use of microcontroller 1 and look-up tables residing in the memory modules 45 while being governed by the closed servo loop modality 53 described in FIG. 8e. The electrical power to operate all the electronics is obtained from the kinetic winder 1900 driving the Faraday generator and stored in a capacitor.

In the final embodiment that the applicant contemplates, the apparatus uses the kinetic winder 500 to power both the electronic circuit 30 as depicted in FIGS. 8a and 8b and disclosed above and the pump 1500 as depicted in FIG. 1a. This embodiment is different from the previous contemplated embodiments in that the energy needed to operate the pump 1500 and the energy needed to drive the electronic circuit 30 come from the same source. The kinetic winder 500 obtains energy form the mechanical movement of the jawbone 50 as disclosed above and depicted in FIG. 9. The energy that is supplied to electronic circuit 30 by the kinetic winder 500 drives the circuit and its various sensor elements as disclosed above. When the circuit 30 has determined that medication is needed in the patient's body, a signal is sent to the pump 1500. The pump 1500 then begins to dispense the medicating agent out of the apparatus as disclosed above using energy obtained by the kinetic winder 500. In other words, the present embodiment envisions that the kinetic winder 500 powers all of the various elements of the claimed apparatus and is coupled to those elements in order to distribute the energy obtained from the movement of jawbone 50.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An implantable apparatus capable of delivering medicating agents directly to the blood stream of a patient's body comprising:
    an artificial dental crown;
    a kinetic mainspring winder disposed within the artificial dental crown;
    a worm gear coupled to and driven by the kinetic mainspring winder; and
    a pump mechanism coupled to and mechanically driven by the worm gear, the pump mechanism directly delivering the medicating agents to the blood stream of the body at a time-measured rate, wherein the pump mechanism comprises a plunger which defines a refillable and a variable volume of a reservoir for holding and dispensing a medicating agent within the artificial crown,
    wherein the plunger is arranged and configured to be driven only in a downward direction by the kinetic mainspring winder and to be driven in an upward direction only by the incoming flow of medicating agent when the reservoir is being refilled, wherein the apparatus comprises a jaw implant, wherein a rotor of the kinetic mainspring winder is asymmetrically weight to be inclined at a 5 degree inclination relative to a plane perpendicular to a longitudinal axis of the artificial dental crown, wherein the longitudinal axis of the artificial dental crown is along the length of the jaw implant from an occlusal end to an apical end.

2. The apparatus of claim 1 where further comprising a threaded implant screw with a perforated delivery duct coupled to the reservoir defined by the pump mechanism for dispensing medicating agents into or near a plurality of adjacent blood vessels in a jaw bone, wherein the reservoir comprises means for refilling the reservoir through and with the dental crown in situ and intact.

3. The apparatus of claim 1 further comprising a timer and clutch mechanism coupled to the pump mechanism via the worm gear for selective dispensing the medicating agent into the body.

* * * * *